United States Patent
Bokrantz et al.

(10) Patent No.: US 11,607,560 B2
(45) Date of Patent: Mar. 21, 2023

(54) SYSTEM, COMPUTER PROGRAM PRODUCT AND METHOD FOR RADIATION THERAPY TREATMENT PLANNING

(71) Applicant: RaySearch Laboratories AB, Stockholm (SE)

(72) Inventors: Rasmus Bokrantz, Enebyberg (SE); Kjell Eriksson, Bålsta (SE); Fredrik Löfman, Lidingö (SE)

(73) Assignee: RaySearch Laboratories AB, Stockholm (SE)

( * ) Notice: Subject to any disclaimer, the term of this patent is extended or adjusted under 35 U.S.C. 154(b) by 0 days.

(21) Appl. No.: 17/612,666

(22) PCT Filed: May 12, 2020

(86) PCT No.: PCT/EP2020/063113
§ 371 (c)(1),
(2) Date: Nov. 19, 2021

(87) PCT Pub. No.: WO2020/234032
PCT Pub. Date: Nov. 26, 2020

(65) Prior Publication Data
US 2022/0241611 A1    Aug. 4, 2022

(30) Foreign Application Priority Data
May 20, 2019  (EP) .................................... 19175437

(51) Int. Cl.
*A61N 5/10* (2006.01)
(52) U.S. Cl.
CPC .................................. *A61N 5/1031* (2013.01)
(58) Field of Classification Search
CPC ..... A61N 5/1031; A61N 5/103; A61N 5/1038
See application file for complete search history.

(56) References Cited

U.S. PATENT DOCUMENTS

2011/0160513 A1    6/2011  Luan et al.
2016/0303398 A1*  10/2016  Eriksson .............. A61N 5/1031
(Continued)

FOREIGN PATENT DOCUMENTS

| CN | 103857439 A | 6/2014 |
| CN | 104519956 A | 4/2015 |

(Continued)

OTHER PUBLICATIONS

First Office Action dated Jun. 7, 2022 in Chinese Patent Application No. 202080037011.0 (5 pages) with an English translation (4 pages).

(Continued)

*Primary Examiner* — Christine H Matthews
*Assistant Examiner* — Joshua Daryl D Lannu
(74) *Attorney, Agent, or Firm* — Faegre Drinker Biddle & Reath LLP

(57) ABSTRACT

Better Pareto dose distributions for multi-criteria optimization of treatment plans can be obtained by obtaining at least one reference dose function designed to result in an acceptable reference dose distribution, defining a multi-criteria optimization problem including the at least one reference dose function as at least one optimization function, performing at least two optimization procedures based on the multi-criteria optimization problem to generate a set of at least two possible treatment plans, obtaining a treatment plan to be used for treating the patient, based on the set of possible treatment plans, by selecting one plan or by combining plans.

14 Claims, 3 Drawing Sheets

(56) References Cited

U.S. PATENT DOCUMENTS

2017/0072221 A1  3/2017  Nord et al.
2018/0043182 A1  2/2018  Wu et al.

FOREIGN PATENT DOCUMENTS

| EP | 3581241 A1 | 12/2019 | |
|----|----|----|----|
| JP | 2016-532530 A | 10/2016 | |
| JP | 2019-510585 A | 4/2019 | |
| JP | 2019-511321 A | 4/2019 | |
| WO | WO-2009/137010 A2 | 11/2009 | |
| WO | WO-2009137010 A2 * | 11/2009 | ............ A61B 90/10 |
| WO | WO-2016/144914 A1 | 9/2016 | |

OTHER PUBLICATIONS

Notice of Reasons for Refusal dated Jun. 28, 2022 in Japanese Patent Application No. 2021-569003 (3 pages) with an English translation (3 pages).

* cited by examiner

SYSTEM, COMPUTER PROGRAM PRODUCT AND METHOD FOR RADIATION THERAPY TREATMENT PLANNING

CROSS REFERENCE TO RELATED APPLICATIONS

This application is a National Stage of International Application No. PCT/EP2020/063113, filed May 12, 2020, and claims the benefit of European Patent Application No. 19175437.3, filed May 20, 2019, the entire contents of each of which are incorporated herein by reference.

TECHNICAL FIELD

The present invention relates to radiation therapy treatment planning, and in particular to such planning involving multi-criteria optimization (MCO).

BACKGROUND

In the field of radiation therapy treatment, a key challenge is to devise a high-quality plan. There is a constant search for improvement to methods of optimizing treatment plans to ensure the desired effect on a target volume such as a tumor while causing as little damage as possible to healthy tissue and preferably no damage at all to organs at risk (OARs), such as the heart or the spinal cord.

One form of treatment plan optimization is multi-criteria optimization (MCO), which enables a clinician to explore different treatment options through a navigation interface. This form of optimization is based on an optimization problem comprising a set of optimization functions. Each optimization function may be an objective function or a constraint. A number of possible treatment plans are obtained based on the optimization functions. Using the possible plans enables multi-criteria treatment planning in real time, by linearly navigating between the plans by adjusting the values of the objective functions.

Radiation therapy treatment planning involving MCO may be performed for different types of radiation therapy, such as external beam radiation therapy based on photons, light ions, or electrons, or brachytherapy. The generation of the possible plans using inverse planning techniques needs to be tailored for each specific treatment technique, whereas the principle of navigation is applicable regardless of treatment technique without specific customizations.

In MCO, an optimization problem including at least two objective functions is used to generate a number of possible treatment plans related to a particular patient case. One of the plans may be selected as the most suitable one. Alternatively, it is known to navigate between the dose distributions of a number of such possible treatment plans to select a navigated dose distribution that may be used to generate a deliverable treatment plan.

To this end, some treatment planning systems have a user interface displaying a number of slider bars to enable the operator to navigate between different dose distributions to select a combination of the dose distributions. In some cases, one favorable dose distribution may be selected. The navigation is preferably carried out within a certain limited range of dose distributions around the initial dose distribution.

The at least two objective functions used in the optimization problem according to MCO are to some extent incompatible in the sense that improvement in one objective requires a deterioration in one or more other objectives. The Pareto surface is composed of the Pareto optimal treatment plans, that is, the feasible plans such that no objective can be improved without a deterioration in at least one of the other. The definition of feasible is determined by the constraints of the MCO problem. The navigation therefore aims at identifying the dose distribution that presents the best compromise between the fulfilment of the different objective functions. European Patent Application EP18177329 A1 discusses the principles of Pareto optimization in greater detail.

The objective functions and constraints used in MCO are based on quality measures for the treatment plan. An objective function measures the deviation of a parameter from a desired value, typically related to the dose distribution, for example, in terms of minimum or maximum dose to a specific organ. A constraint comprises a quality measure and an associated set of feasible values. The quality measures used as objectives functions and in constraints should have mathematical properties that make them suitable for optimization, such as continuity and differentiability. The quality measures used as objective functions and in constraints are typically penalties, such as quadratic penalties, on the deviation between the actual voxel dose to a structure and a reference dose level.

User interfaces have been developed that allow an operator to adjust the desired value for each objective function. One slider bar is provided for each objective function, and the operator can manipulate the slider bars. The slider movements are translated to changes of weighting of the dose distributions by a navigation algorithm that takes desired objective function values as input. To facilitate the navigation, clamps may be applied to restrict the possible range of slider movements. In the simplest embodiment, a clamp functions as an upper bound for the objective function value associated with a slider.

Since a radiation therapy treatment plan has an associated dose distribution, the dose distributions of the possible treatment plans defining the approximation of the Pareto surface will be referred to in this document as Pareto dose distributions. When the Pareto surface has been defined or approximated, the actual dose planning may be performed by linear interpolation of the Pareto dose distributions, to produce a navigated dose distribution Efficient MCO requires good input data, including a well-defined optimization problem and input treatment plans that will ensure a satisfactory result. It is a challenge to provide treatment plans to navigate between that are clinically relevant, that is, that will result in a dose distribution that is acceptable for delivery to the patient. This will in turn enable a satisfactory result to be achieved with the use of a limited number of treatment plans, making the navigation more efficient.

US 2017/0072221 discloses the generation of a Pareto surface using an objective identifying module which creates MCO objective functions or constraints that measure qualities of a plurality of sample plans being generated from a knowledge base containing previous treatment plans.

SUMMARY

It is an object of the present invention to provide an improved way of providing a collection of possible treatment plans for a given patient case, which may be used as they are or as input plans for MCO navigation.

The invention relates to a method of generating a radiation therapy treatment plan, A method of generating a radiation therapy treatment plan for a volume of a patient to be treated, comprising the following steps performed in a computer:

obtaining at least one reference dose function designed to result in a reference dose distribution, said reference dose distribution being an acceptable dose distribution for the volume, said reference dose function being designed to minimize the difference between a resulting dose distribution and the reference dose distribution, defining a multi-criteria optimization problem including the at least one reference dose function as at least one optimization function, performing at least two optimization procedures based on the multi-criteria optimization problem to generate a set of at least two possible treatment plans, obtaining a treatment plan to be used for treating the patient, based on the set of possible treatment plans.

This method ensures that the treatment planning is based on one or more reference dose distributions that are clinically acceptable for delivery to a patient. This enables the generation of a set of possible treatment plans that are clinically relevant and that may have a sufficiently high quality for use in treatment of the patient without any further adjustment. It also facilitates MCO navigation between the plans for further adjustment, in that the possible dose distributions used in the MCO navigation clinically relevant in the sense that they are all guaranteed to be within a suitable range of dose distributions.

According to a preferred embodiment of the invention, an input dose distribution is provided, which has been deemed to be a suitable dose distribution for the irradiated volume. The input dose distribution is preferably a clinically deliverable dose distribution, for example, obtained from an existing treatment plan for the patient to be treated. The input dose distribution can also be an estimated dose distribution obtained, for example, from a dose prediction algorithm Clinically deliverable means that the treatment delivery system is technically able to deliver the dose distribution.

The reference dose function corresponding to a reference dose distribution may, in preferred embodiments be generated in the following way: A confidence interval is defined around the input dose distribution, limiting the possible deviations of the reference dose distributions from the input dose distribution. One or more reference dose distributions are defined within the confidence interval and a reference dose function is defined for each reference dose distribution. Preferably a number of reference functions are generated, each based on a reference dose distribution where the reference dose distributions are different from each other. Each reference dose function may be formulated as an objective function that penalizes differences between a resulting dose distribution and a given reference dose distribution, or as a constraint. The reference dose function is included in the optimization problem. The optimization problem may comprise only reference dose functions related to reference dose distributions but will normally comprise one or more other optimization functions.

The use of a reference dose function as defined means that the full spatial dose distribution can be taken into account so that the deviation of the resulting dose distribution from the input dose distribution can be measured more realistically. The qualities of the input dose distribution are thereby preserved better when generating alternative plans compared to if deviation is measured in terms of function value of standard optimization functions. In particular, dose shape preferences that are not measurable with standard optimization functions can be taken into account.

The other objective functions, that is, the ones not related to a reference dose distribution, may be related to clinical goals, be created from a template, or selected manually. They may, for example prescribe a reduced dose to an organ at risk, improve coverage and uniformity for all targets or improve the conformity of the dose to a target.

A set of plans that are preferably Pareto optimal are generated by iterations of the optimization process based on the MCO problem. Several well-known techniques exist for generation of a Pareto surface representation, such as the weighted sum method or the epsilon constraint method. Accordingly, the optimization procedure may be performed so as to generate a set of Pareto optimal possible treatment plans and the step of obtaining a treatment plan comprises navigating between the dose distributions corresponding to at least two possible treatment plans and generating a plan based on the result of the navigation.

The set of plans are used to select or generate a radiation therapy treatment plan. This may involve presenting the set of plans as discrete alternatives and subsequently selecting one of the plans, or using the set of plans as input to an MCO navigation for fine tuning. In the latter case, the step of obtaining a treatment plan comprises navigating between dose distributions corresponding to at least two possible treatment plans and generating a plan based on the result of the navigation. The dose distributions in this case are preferably Pareto dose distributions as defined above. In some embodiments, there is a step evaluating the quality of each plan in the set of plans to decide if one of the plans can be used as it is, or if MCO navigation should be performed. In dependence of the result of the evaluation, it is decided whether to select one of the possible treatment plans as the plan to be used or to obtain a treatment plan by navigating between dose distributions corresponding to at least two possible treatment plans and generating a plan based on the result of the navigation.

The method according to the invention can be used for fine tuning of treatment plans, which may be of particular interest for treatment plans that are automatically generated.

If the set of plans is used as input to an MCO navigation, the final treatment plan to be used may be obtained by fine tuning between the reference dose distributions corresponding to Pareto optimal treatment plans.

The inventive method is not dependent on the hardware used for treatment delivery. The method is, therefore, equally valid for any treatment technique where multi-criteria optimization is applicable, e.g. external beam photon therapy, electron therapy, ion beam therapy, and brachytherapy.

The invention also relates to a computer program product comprising computer readable code means, preferably on a non-transitory storage means, which, when run in the processor of a computer system, will cause the computer system to perform the method according to any one of the preceding claims. The invention also relates to a computer system comprising a processor and a program memory, said program memory comprising a such a computer program.

BRIEF DESCRIPTION OF THE DRAWINGS

The invention will be described in more detail in the following, by way of example and with reference to the appended drawings, in which.

DETAILED DESCRIPTION

Figure 1:
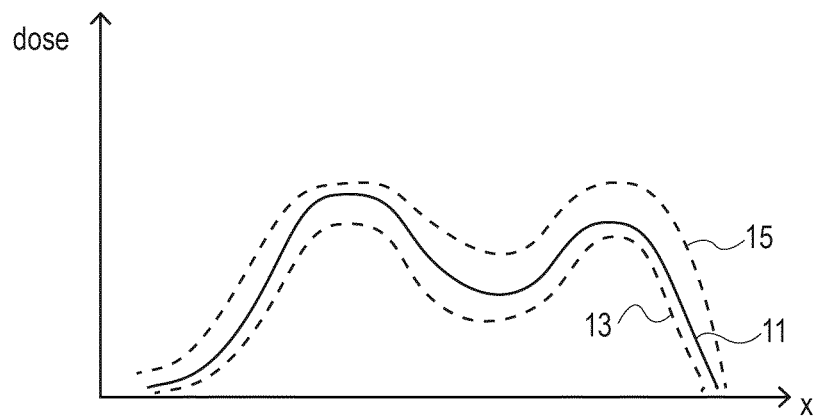
FIG. 1 illustrates the relationship between an input dose distribution, a confidence interval and a reference dose function.

FIG. 1 is a two-dimensional coordinate system illustrating a dose distribution as a function of the position along the x-axis. It should be understood that FIG. 1 is merely a simplified example of an input dose distribution and a way of specifying a confidence measure, provided for illustrative purposes. Normally, a dose distribution will be three-dimensional. A first, solid line 11 illustrates the input dose distribution. The input dose distribution should be a realistic dose distribution, that is one that may actually be achieved, in contrast to an ideal dose distribution often used for planning, which involves ideal doses to each region of the patient but is far from anything that may be achieved in reality. The input dose distribution may be, for example, the resulting dose of an existing treatment plan, an imported dose distribution, an estimated dose distribution from a dose prediction algorithm for automatic planning, or the dose of a previously treated patient.

The confidence measure should preferably be defined in terms of intervals of feasible deviations per voxel of the patient volume. In FIG. 1, dashed lines 13, 15, one on each side of the solid line, delimit a confidence interval around the input dose distribution, which specifies how large deviations from the input dose distribution are to be allowed, that is, the acceptable values for the reference dose distributions. As can be seen, the confidence interval can have different widths at different positions along the x-axis. This corresponds to a high precision in areas where the confidence interval is narrow, that is, the distance between the dashed lines for a given position, in FIG. 1, a given value of x, is narrow. In the case of automatic planning, the confidence measure underlying the confidence interval can be obtained as a byproduct of the dose prediction. For example, if the dose prediction is created by taking the majority vote of a forest of decision trees, the confidence measure may be based on the variability observed across the individual trees. If the dose prediction is based on a neural network, the uncertainty in the prediction may be estimated by introducing perturbations to the network (e.g., randomly disconnecting links between nodes) and analyzing the resulting variability in the prediction. Alternatively, the confidence interval can be specified by a manual user.

According to embodiments of the invention, one or more reference dose distributions are defined within the confidence interval. One suitable possible reference dose distribution is the one that follows exactly the lower dashed line 13, corresponding to the lowest dose within the confidence interval, that is, the lowest possible dose distribution. Such a reference dose distribution may be used to generate a reference dose function used as an objective function for an organ at risk (OAR), since lower doses are always preferable for OARs. A reference dose distribution corresponding to the highest dose within the confidence interval may, similarly, be used to generate a constraint for an OAR, the constraint then corresponding to the minimal acceptable level of sparing for the OAR. Objectives and constraints for target structures may in similar fashion be defined by selecting reference dose distributions within the confidence interval that will limit the deviation from the prescription dose level or push the reference dose distribution towards an idealized target dose, or a combination of these. For example, reference dose distributions that are as close to the prescription dose level of the target as possible, or as far from the prescription dose level as possible may be selected. A reference dose distribution may also coincide with the input dose distribution 11. The total number of reference dose distributions may be selected freely, for example 10 reference dose distributions may be defined.

Each reference dose distribution is used to formulate a reference dose function, which is an objective function, or a constraint designed to achieve that reference dose distribution. Thus, a reference dose function measures the nearness of a resulting dose distribution to the reference dose distribution associated with the reference dose function. A reference dose function may measure differences between then resulting dose distribution and the reference dose distribution on a voxel per voxel level. Similarly, less conservative reference dose functions may be defined by measuring differences between clusters of voxels. For example, clusters of voxels may be defined based on the proximity to points in the patient volume or based on proximity to the target volume. The average doses of such clusters may then be compared. Clusters may also be formed based on voxels that receive a similar dose according to the input dose distribution. A reference dose function may also be based on other spatial measures of similarity between dose distributions, such as a gamma function used for treatment plan quality assurance, or other measures of similarity between pixelated images.

Often, a reference dose function is restricted to act only on a set of voxels associated with a given region of interest (ROI). A reference dose function can also be a composite function defined as a weighted sum of multiple constituent reference dose functions. It should be noted that the reference dose functions measure nearness over the whole spatial dose distribution as opposed to a standard optimization function, which measures similarity with respect to a point characteristic, such as a dose-volume histogram (DVH) point or an average dose value.

Figure 2:
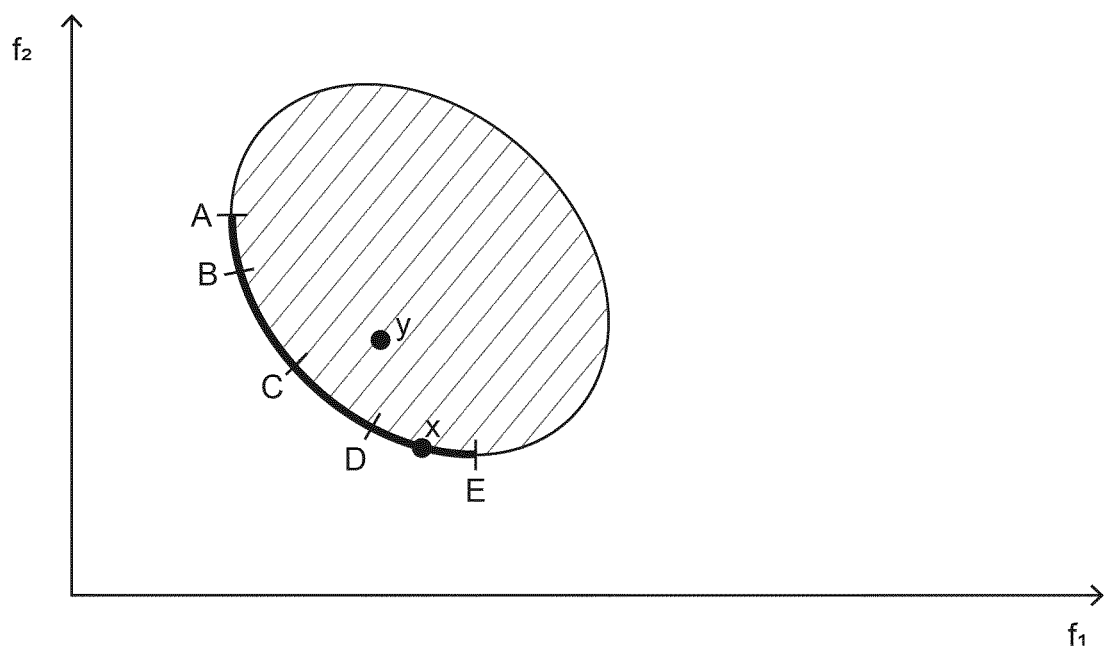
FIG. 2 illustrates a two-dimensional Pareto surface.

FIG. 2 illustrates the principle of multi-criteria optimization for a simplified set of objective functions. In MCO, a multi-criteria optimization problem is defined in terms of a set of objective functions and a set of constraints. As explained above, according to the invention, at least one objective function and/or at least one constraint is a reference dose function as defined above.

This is illustrated in FIG. 2 using only two objective functions $f_1$ and $f_2$ (both to be minimized), respectively, to enable a two-dimensional display. In a practical case the number of objective functions may typically be between around 10, which would require a multi-dimensional space. The area enclosed by the ellipse represents objective function vectors that correspond to solutions that are feasible with respect to the constraints.

The curve in thick solid indicates the vectors of objective function values corresponding to Pareto optimal solutions defining achievable combinations of the two objective functions $f_1$ and $f_2$. The curve is known in multi-criteria optimization as the Pareto surface. In the general case, the Pareto surface will be a surface in an N-dimensional space, where N is the number of objective functions. As can be seen, in any point on the Pareto surface an improvement of one of the objective functions will lead to a deterioration of the other one. Any chosen combination of the objective functions will be a trade-off based on the desired result.

The system comprises a number of Pareto dose distributions, each of which will lead to a point on the Pareto surface. In this example, there are five Pareto dose distributions, each with a corresponding point A, B, C, D, E on the Pareto surface. For point A, the second objective function $f_2$ has a high value but the first objective function $f_1$ has a low value, which is more desirable. For point E, the first objective function $f_1$ has a high, poorer value but the second objective function $f_2$ has a low, better value, compared to point A. For the intermediary points B, C, D the values of both objective functions are between the ones for the outermost points A and E. FIG. 2 also shows a point x which is interpolated between points D and E, by a weighted sum of the dose distributions generating these two points.

At the essence of multi-criteria optimization is finding the point on the closed curve or inside the shaded region, in other words, the weighted sum of all the Pareto dose distributions, that will result in best possible clinical outcome for the patient. As the exact outcome is unknown at the timepoint when the navigated dose distribution is selected, the selection of the most preferred plan is an in-part subjective choice on the behalf of the clinicians. This may be a point on the Pareto surface, or a point within the region defined by all feasible solutions, the latter being indicated by a point y inside the region.

Figure 3:
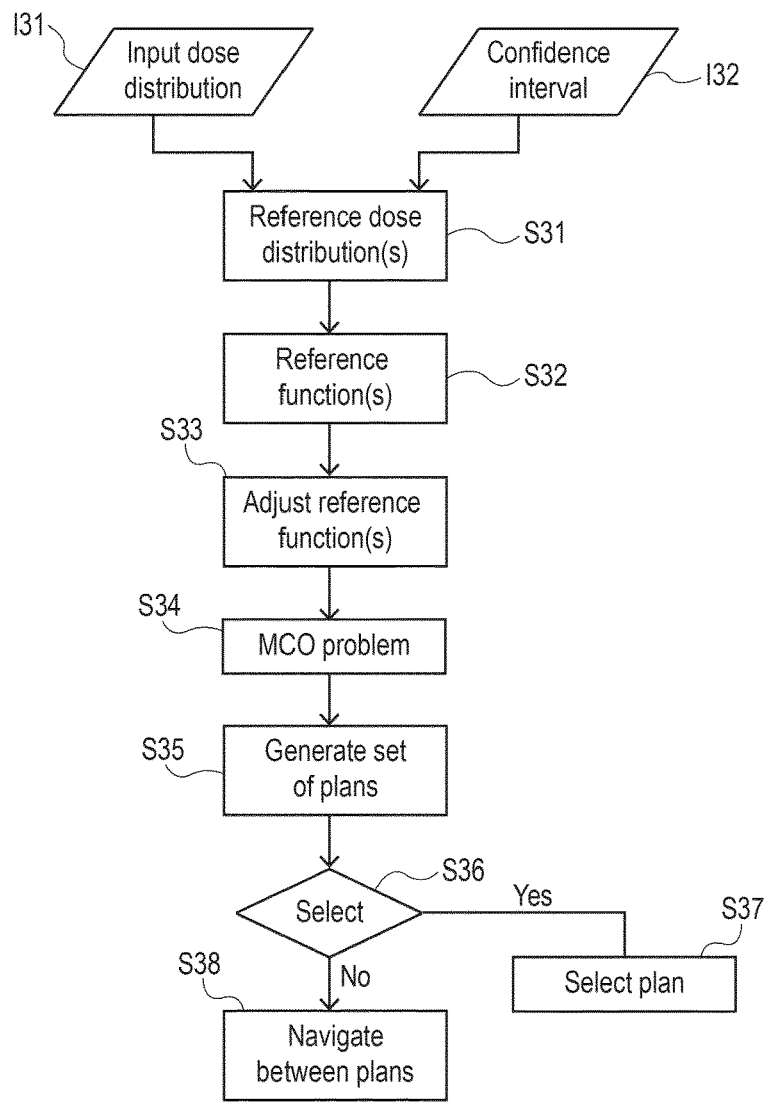
FIG. 3 is a flow chart of a method according to the invention.

FIG. 3 is a flow chart of a method according to an embodiment of the invention, with reference to the concepts discussed in connection with FIG. 1. Input data to the method are an input dose distribution 131 and a confidence interval 132 around the input dose distribution. The input dose distribution and confidence interval are as discussed in connection with FIG. 1, and may be provided obtained together or sequentially, in any suitable way.

In a step S31, one or more reference dose distributions are obtained, for example, by sampling within the confidence interval. As discussed in connection with FIG. 1, the reference dose distributions are possible dose distributions within the confidence interval. In step S32, a reference dose function is defined for each of the reference dose distributions obtained in step S31. As will be understood, a set of reference dose functions to be used in the following steps may be obtained in any suitable way, as long as each reference dose function results in a dose distribution that has been found to be within acceptable limits.

Step S33 is an optional step in which the reference dose functions can be adjusted in the sense that a different reference dose distribution may be selected and a reference dose function may be generated for this newly selected dose distribution. Example of adjustments are shifts of the reference values, such as shifts of the reference dose or adjustments of constraints such that reference dose function values within some positive upper bound are considered feasible. The magnitude of the shifts may be based on user input or a prediction accuracy calculated by a dose prediction algorithm, so that larger shifts are allowed in regions where the dose prediction is uncertain. Regions may be spatial that is, including voxels that are located close to each other, or dose-based, that is, including voxels that have similar doses assigned to them.

In step S34, an MCO problem is defined. As explained above, an MCO problem is an optimization problem including at least two objective functions and a set of constraints, which may be empty. In this case, the MCO problem includes the reference dose function or functions obtained in step S32 as objective functions or as constraints, and possibly other objective functions and constraints. The MCO problem may also include information for each reference dose function related to how much the associated reference dose distribution deviates from the input dose distribution.

Mathematically, the MCO problem is defined as in the introduction, that is, $$\text{Minimize } [f_1(x), f_2(x), \ldots, f_N(x)]^T$$
$$\text{Subject to } x \text{ in } X,$$

where the feasible set X is defined by a number of constraint functions c, according to $$X = \{x : c_i(x) \leq 0\}, i = 1, \ldots, m.$$

The vector x is the vector of optimization variables used in the optimizations where the precalculated plans that form the representation of the Pareto surface are generated. Note that the definition of the right-hand side of the constraints as zero is without loss of generality.

The optimization of a single treatment plan is performed with respect to a scalarized counterpart of the MCO problem, e.g., a weighted sum formulation according to:

$$\text{Minimize } \sum_{i=1,\ldots,N} w_i f_i(x)$$
$$\text{Subject to } x \text{ in } X.$$

The weights $w_i$ may be varied between each optimization to generate plans from different parts of the Pareto surface. As is well known, other scalarization techniques than the weighted sum method may also be used, e.g., the epsilon constraint method.

In step S35 a set of possible treatment plans are generated through optimization based on the MCO problem defined in step S33. Preferably, the possible treatment plans are Pareto optimal with respect to the MCO problem. Several well-known techniques exist for generation of Pareto surface representation, such as the weighted sum method or the epsilon constraint method. This is an iterative process, which involves running the optimization process a number of times, generating a possible treatment plan in each iteration.

The set of possible treatment plans is used to determine a treatment plan. In the simplest case, one of the possible treatment plans is selected. FIG. 3 illustrates a decision step S36 to determine if one of the possible treatment plans is sufficiently good to be used without modification. If yes, go to step S37; if no, go to step S38.

In step S37 one possible treatment plan that is considered sufficiently good is selected to be used when treating the patient. In step S38, instead, the set of possible treatment plans is used to generate an improved treatment plan. This is typically done by MCO navigation between some or all of the possible treatment plans as discussed in connection with FIG. 2. It is possible to go directly to step S37 or step S38 by default, without the decision step S36.

The reference dose distribution is preferably a fixed parameter in the optimization. If the confidence measure is specified as confidence intervals per voxel, then the reference distribution could be sampled from a distribution of possible deviations over the confidence intervals. If multiple reference dose functions are used, each reference dose function may have a distinct reference dose distribution.

The optimization variables x depend on the type of radiation treatment method. Standard optimization variables for photon therapy techniques are energy fluences per bixel of each beam, a bixel being defined as a surface element in the beam cross-sections, or multi-leaf collimator leaf positions and number of monitor units (MUs) for each segment of each beam. Standard optimization variables for scanned ion therapy are number of MUs per scanning spot of each beam. In the previous discussion the confidence interval has been treated as a uniform interval around the input dose distribution, without any specification of the probability of the dose being found across the interval. It is also possible, as illustrated in FIG. 4, to consider different probabilities for different doses for each voxel.

Figure 4:
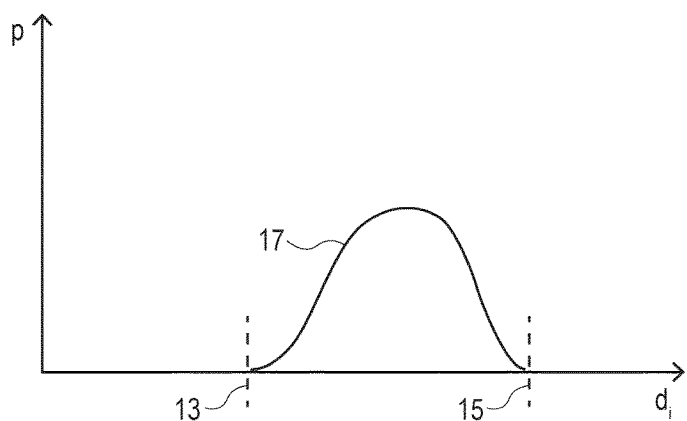
FIG. 4 illustrates the use of probabilities within the confidence interval.

FIG. 4 is a coordinate system displaying as a curve 17 the probability density p that the dose in a certain voxel i attains a certain value $d_i$, the voxel being a volume element inside the treatment volume. The upper and lower limits of the confidence interval are marked on the x-axis and represented by dashed lines 13 and 15. The integral of the curve 17 between the limits 13, 15 by definition equals 1. This probability distribution can be taken into account in the inventive method by selecting the reference dose distributions in accordance with the probability of the respective doses for each voxel.

Figure 5:
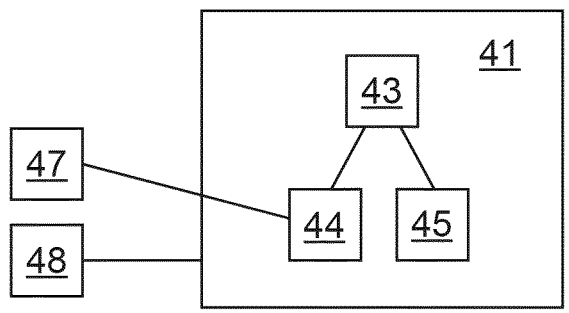
FIG. 5 illustrates a computer system in which the inventive method may be implemented.

FIG. 5 is a schematic representation of a computer system in which the inventive method may be performed. A computer 41 comprises a processor 43, connected to a first and a second data memory 44, 47 and a program memory 45. Preferably, one or more user input means 48 are also present, in the form of a keyboard, a mouse, a joystick, voice recognition means or any other available user input means. The user input means may also be arranged to receive data from an external memory unit.

The first data memory 44 comprises necessary data for performing the method, and applicable thresholds and limits. The second data memory 47 holds data related to one or more current patients for which treatment plans are to be developed. The program memory 45 holds a computer program arranged to make the computer perform the method steps, for example, as discussed in connection with FIG. 3.

As will be understood, the data memories 44, 47 as well as the program memory 45 are shown and discussed schematically. There may be several data memory units, each holding one or more different types of data, or one data memory holding all data in a suitably structured way, and the same holds for the program memories.

The invention claimed is:

1. A method of generating a radiation therapy treatment plan for a volume of a patient to be treated, comprising the following steps performed in a computer:
obtaining at least one reference dose function corresponding to a reference dose distribution, said reference dose distribution being an acceptable dose distribution for the volume, said at least one reference dose function being designed to minimize a difference between a resulting dose distribution and the reference dose distribution;
defining a multi-criteria optimization problem including the at least one reference dose function as at least one optimization function;
performing at least two computer-based optimization procedures based on the multi-criteria optimization problem to generate a set of at least two possible treatment plans comprising Pareto optimal possible treatment plans; and
obtaining a treatment plan to be used for treating the patient, based on the set of possible treatment plans.

2. A method according to claim 1, further comprising a step of generating each reference dose function corresponding to the reference dose distribution by:
providing a confidence interval indicating an acceptable range of dose distributions for the volume;
generating the reference dose distribution, said reference dose distribution being within the confidence interval; and
generating the at least one reference dose function based on the reference dose distribution.

3. A method according to claim 2, wherein the step of providing the confidence interval comprises the step of providing an input dose distribution and defining an interval around the input dose distribution as the confidence interval.

4. A method according to claim 3, wherein the input dose distribution is a dose distribution, which is a clinically deliverable dose distribution obtained from an existing treatment plan for the patient to be treated.

5. A method according to claim 3, wherein the input dose distribution is an estimated dose distribution obtained from a dose prediction algorithm.

6. A method according to claim 1, wherein the step of obtaining a treatment plan comprises selecting one of the possible treatment plans as the treatment plan to be used.

7. A method according to claim 1, wherein the at least two possible treatment plans have corresponding dose distributions, wherein the step of obtaining the treatment plan comprises:
navigating between the corresponding dose distributions of the at least two possible treatment plans; and
generating the treatment plan based on the navigating between the reference dose distributions.

8. A method according to claim 1, wherein the at least two possible treatment plans have corresponding dose distributions, further comprising a step of evaluating a quality of at least one of the possible treatment plans and, based on the evaluating, either:
selecting one of the possible treatment plans as the treatment plan to be used, or
obtaining the treatment plan to be used by navigating between the corresponding dose distributions of the at least two possible treatment plans; and
generating the treatment plan to be used based on the navigating between the corresponding dose distributions of the at least two possible treatment plans.

9. A method according to claim 1, wherein the Pareto optimal possible treatment plans have corresponding dose distributions, wherein the step of obtaining the treatment plan comprises:
navigating between the corresponding dose distributions of the Pareto optimal possible treatment plans; and
generating the treatment plan to be used based on the navigating between the corresponding dose distributions of the Pareto optimal possible treatment plans.

10. A method according to claim 1, wherein the at least one optimization function comprises an objective function.

11. A method according to claim 1, wherein the at least one optimization function comprises a constraint.

12. A method according to claim 1, wherein the at least one reference dose function comprises at least a first reference function and a second reference function, the reference dose distribution comprises a first reference dose distribution and a second reference dose distribution, and the method further comprises generating the first reference function and the second reference function based on the first reference dose distribution and the second reference dose distribution, respectively.

13. A computer program product comprising a processor and a non-transitory computer readable medium storing computer readable code, which, when run in the processor of a computer system, will cause the computer system to perform the method according to claim 1.

14. A computer system comprising a processor and a program memory, said program memory comprising a computer program product according to claim 13.

* * * * *